United States Patent [19]

Simeone et al.

[11] Patent Number: 5,623,037
[45] Date of Patent: Apr. 22, 1997

[54] COATINGS BASED ON PERFLUOROPOLYETHERS CONTAINING ACRYLIC GROUPS

[75] Inventors: Giovanni Simeone, Solaro; Claudio Tonelli, Concorezzo; Ezio Strepparola, Treviglio; Fabrizio Mutta, Caronno Pertusella, all of Italy

[73] Assignee: Ausimont S.p.A., Milan, Italy

[21] Appl. No.: 234,912

[22] Filed: Apr. 28, 1994

[30] Foreign Application Priority Data

Apr. 28, 1993 [IT] Italy .................. MI93A0837

[51] Int. Cl.$^6$ .................................................. C08F 16/24
[52] U.S. Cl. ................................................................ 526/247
[58] Field of Search ............................................ 526/247

[56] References Cited

U.S. PATENT DOCUMENTS

| | | |
|---|---|---|
| 3,242,218 | 3/1966 | Miller et al. . |
| 3,513,203 | 5/1970 | Sianesi et al. . |
| 3,665,041 | 5/1972 | Sianesi et al. . |
| 3,810,874 | 5/1974 | Mitsch et al. . |
| 3,847,978 | 11/1974 | Sianesi et al. . |
| 5,011,979 | 4/1991 | Gregorio et al. . |

FOREIGN PATENT DOCUMENTS

| | | |
|---|---|---|
| 373385 | 6/1990 | European Pat. Off. . |
| 394927 | 10/1990 | European Pat. Off. . |
| 393230 | 10/1990 | European Pat. Off. . |
| 1104482 | 2/1968 | United Kingdom . |

OTHER PUBLICATIONS

JP63068542; 1988 Mar. 28 Takaai et al "Fluorine Containing Methacrylate Esters" pp. 1–7.
Derwent Abstract for JP 63–068542.
"Effects of Water–Soluble Spacers on the Hydrophobic Association of Fluorocarbon Modified Polyacrylamide," F.S. Hwang and T.E. Hogen–Esch, *Polymer Preparations* vol. 34, No. 1 pp. 404–406 (1993).
European Search Report for EP 94106375, Dec. 13, 1994.

*Primary Examiner*—Joseph L. Schofer
*Assistant Examiner*—N. Sarofim
*Attorney, Agent, or Firm*—Bryan Cave LLP

[57] ABSTRACT

Coatings based on perfluoropolyethers terminated with acrylic groups and containing ethoxylic groups as a connecting bridge between the fluorinated part and the (meth)acrylic group.

4 Claims, No Drawings

COATINGS BASED ON PERFLUOROPOLYETHERS CONTAINING ACRYLIC GROUPS

The present invention relates to coatings based on PFPE (perfluoropolyethers) having high mechanical properties, in particular hardness, combined with high resistance to photooxidative degradation and resistance to hydrolysis.

These properties are required in all applications as top-coat, for instance in the car industry.

Fluorinated polyacrylates from perfluoropolyethers, in particular Galden® acrylates, are known (see U.S. Pat. No. 5,011,979).

Experiments carried out from the Applicant have pointed out that resins obtained therefrom have such poor resistance properties to hydrolysis, as to make them unsuitable to the application as top-coat.

It has been unexpectedly found that it is possible to prepare coatings based on PFPE having the above indicated properties by utilizing the PFPE of the invention as hereinafter specified.

Object of the present invention are perfluoropolyethers containing (meth)acrylic groups of general formula:

$$YCF_2OR_fCFXCH_2(OCH_2CH_2)_pOCOCR=CH_2 \quad (I)$$

where Y=F, Cl, $CF_3$, $C_2F_5$, $C_3F_7$, $C_4F_9$; and X=F, $CF_3$; where p is an integer from 1 to 5; $R_f$ represents a radical having perfluoropolyethereal structure of average molecular weight of from 400 to 3000, consisting of sequences of oxyfluoroalkylenic units, such as for instance the units:

—$CF_2O$—, —$CF_2CF_2O$—, —$CF_2CF_2CF_2O$—,

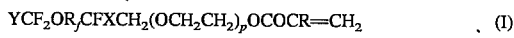

—$CF_2CF_2CH_2O$—;

R=H, $CH_3$.

The acrylated perfluoropolyethers of the present invention can be obtained by using the method indicated in the U.S. Pat. No. 5,011,979 which is here wholly incorporated.

The methods to prepare the precursors are largely known in the art, see for instance U.S. Pat. Nos. 3,513,203; 3,847,978; 3,810,874.

In particular suitable perfluoropolyethers to obtain the present perfluoropolyethers acrylates are the ones formed by sequences of perfluorooxyalkylenic units of the following types:

IA)

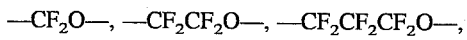

(CFXO) with X=F or $CF_3$, said units being randomly distributed along the perfluoropolyethereal chain;

IIA) ($CF_2CF_2O$),

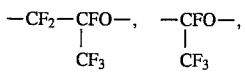

(CFXO) with X=F or $CF_3$, said units being randomly distributed along the perfluoropolyethereal chain;

IIIA)

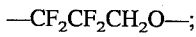

IVA) ($CH_2CF_2CF_2O$);
VA) ($CF_2CF_2CF_2O$);
VIA) ($CF_2CF_2O$).

The perfluoroethereal compounds containing the indicated units are preferably selected among the following classes:

IB) $A'O(C_3F_6O)_m(CFXO)_n$—
  where X is —F, —$CF_3$;
  A' is —$CF_3$, —$C_2F_5$, —$C_3F_7$
  the $C_3F_6O$ and CFXO units are randomly distributed along the perfluoropolyether chain, m and n are integers, the ratio m/n is $\geq 2$.

These perfluoropolyethers are obtained by photooxidation of hexafluoropropene according to the process described in GB Patent 1,104,482.

IIB) $C_3F_7O(C_3F_6O)_m$—, where m is a positive integer whereby the molecular weight has the above indicated value.

They are obtained by ionic telomerization of the hexafluoropropene epoxide. See for instance U.S. Pat. No. 3,242,218.

IIIB) $(C_3F_6O)_m(C_2F_4O)_n(CFXO)_q$ where
  X is equal to —F, —$CF_3$; m, n and q, different from zero, are integers whereby the average molecular weight is at least 400.

These products are obtained by photooxidations of mixtures of $C_3F_6$ and $C_3F_4$ according to the process described in U.S. Pat. No. 3,665,041.

The Applicant has unexpectedly and surprisingly found that the $(CH_2CH_2O)_p$ group of the unsaturated ester, introduced in the formula of the starting alcohol (III) reported below, confers a surprising stability to the ester itself, mainly as regards the non hydrolyzability. Moreover a better reactivity in synthesis phase has been found.

The perfluoropolyethereal part has preferably the following formula:

$$Y—CF_2O(C_3F_6O)_m(CFXO)_nCFX— \quad (II)$$

where Y=F, Cl, $CF_3$, $C_3F_5$ X=F, $CF_3$; m and n have the above indicated meaning in (IIIB)

When Y is different from F or perfluoroalkyl, it can be obtained for instance according to EP Patent 0393230.

The acrylate or methacrylate (I) is prepared by reacting the fluorinated alcohol of formula $$YCF_2OR_fCFXCH_2(OCH_2CH_2)_pOH \quad (III)$$

where X and Y have the meaning indicated, obtained by ethoxylation with ethylene oxide, for instance according to the process of the U.S. Pat. No. 3,810,874, with acrylic or methacrylic acid according to U.S. Pat. No. 5,011,979.

This preparation method is applicable to all alcohols with the other above indicated $R_f$ groups.

The esterification is carried out at a temperature between 30° and 150° C., preferably between 60° and 100° C. in the presence of an usual esterification catalyst as p-toluenesulphonic acid, sulphuric acid, borotrifluoride, phosphoric acid or phosphoric anhydride, in an inert solvent as benzene, toluene, xylene. It is preferable to operate in the presence of polymerization inhibitors such as hydroquinone, di-ter-butyl-p-cresol, ter-butylcatecol, p-methoxy-phenol, etc. in amounts from 0.5 to 3% by weight on the total weight of the reactants.

Alternatively, the acrylate or methacrylate (I) can be prepared by direct reaction of the fluorinated alcohol (III) with acryloyl chloride or metacryloyl chloride, respectively. The reaction is carried out at a temperature comprised between 5° and 60° C. in the presence of a polymerization inhibitor, as reported above. As acid acceptor it can be used a basic substance such as triethyl amine, pyridine, etc. Alternatively, the acrylate or methacrylate (I) can be prepared by reacting the fluorinated alcohol (III) with acrylic or methacrylic anhydride, respectively, at a temperature between 5° and 60° C. in the presence of a polymerization inhibitor and of an acid acceptor.

The fluorine containing acrylic or methacrylic polymer to be utilized as coating is obtained by homopolymerization of the acrylic or methacrylic monomer represented by the structure (I).

Alternatively, it is possible to prepare the polymer by copolymerization from 10 to 90% by moles of the acrylic or methacrylic monomer (I) and from 90 to 10% by moles of one or more monomers represented by the formula

$$CH_2=CR-COO-A \qquad (IV)$$

where R=H, $CH_3$, F, Cl

A is an alkyl from 1 to 12 carbon atoms or a fluoroalkyl from 1 to 10 carbon atoms or an aliphatic or aromatic cyclic group from 6 to 8 carbon atoms.

Alternatively, it is possible to prepare the polymer by copolymerization from 50 to 98% by moles of the acrylic or methacrylic monomer (I) and from 2 to 50% by moles of one or more acrylic monomers represented by the structure

$$CH_2=CR-CO-W-B \qquad (V)$$

where R=H, $CH_3$, F, Cl; W=O, NH; B=H, $(CH_2)_s B_1$ with s=1–5 and $B_1$=—COOH, —OH, —CH=$CH_2$, —NCO —CO—$CH_2$CO—CH, —Si(OR)$_3$ with R alkylic groups from 1 to 5 carbon atoms. It is also possible to prepare the polymer by copolymerization from 1 to 50% by moles of the acrylic monomer (I), from 40 to 90% by moles of one or more monomers represented by the structure (IV) and from 2 to 30% by moles of one or more monomers represented by the structure (V).

The polymer of the present invention to be utilized as coating is obtained by radicalic polymerization in mass, in solution, in suspension or in emulsion.

Examples of usual solvents for the polymerization in solution are fluorinated solvents such as m-hexafluoroxylene, trifluorotoluene and the like, hydrogenated solvents as acetone, methylethylketone, methylisobutylketone (MIBK), ethyl acetate, isobutylacetate, toluene, xylene and the like. The polymer obtained by polymerization in solution can be used under the form of solution prepared by separating the polymer from the reaction solvent and by redissolving the polymer in the same or in another solvent or mixture of solvents, or under the form of solution merely prepared by diluting the resulting reaction mixture with the same or with another solvent or mixture of solvents.

The polymer obtained by polymerization in mass is used by dissolving it in a solvent or mixture of solvents after drying to remove the possibly remaining monomers.

Examples of usual radical polymerization initiators for polymerization in mass, solution or suspension are organic peroxides such as benzoyl peroxide, dicumyl peroxide, lauryl peroxide and the like, azocompounds such as azobisisobutyrronitrile (AIBN), azobisisovaleronitrile and the like.

Examples of usual polymerization initiators for polymerization in emulsion are oxidizing agents, such as ammonium persulphate and potassium persulphate, and redox initiators comprising such an oxidizing agent, sodium sulphite or the like as reducing agent and FE (III) sulphate or similar transition metals salts.

The polymerization initiator is used in amounts from 0.1 to 5% by weight on the weight of all the monomers. Examples of usual emulsifying agents for polymerization in emulsion are of the anionic type, such as sodium lauryl sulphate, ammonium perfluorooctanoate and the like, of cationic type such as dodecyl trimethyl ammonium bromide, hexadecyl trimethyl ammonium bromide and the like, of non-ionic type such as polyethylenoxide lauryl ether and the like; the emulsifying agents are used in amounts of about 0.001 to 5% by weight with respect to the water amount.

If the solvent itself or other features are not sufficient to control the molecular weight, small amounts of chain controlling agents, such as alkanthiols having from 4 to 12 carbon atoms, can be used.

The polymerization temperature is preferably comprised between 30° and 150° C. The fluorinated polymer of the present invention has a molecular weight between 2,000 and 50,000, measured by GPC by using polystyrene as standard.

When the polymer of the present invention contains one or more monomers represented by the structure (V), it is submitted to crosslinking to increase the adhesion to the substrate and its mechanical properties.

Examples of crosslinking agents generally used when the functional group of the monomer (V) is the —COOH group, are compounds having at least two aminic groups such as ethylene diamine, hexamethylenediamine, triethylenediamine, diaminodiphenylmethane and the like; compounds with at least two epoxidic groups such as butylenediglycidyl ether, bisphenol A diglycidyl ether and the like. Examples of crosslinking agents generally used when the functional group of the monomer (V) is the —OH group, are compounds with at least two isocyanic groups such as hexamethylene diisocyanate, isophoronediisocyanate and their trimers or biurets; moreover, there can be used "blocked" polyisocyanates where the blocking agent can be of phenolic, alcoholic, mercaptan, oxime, imino type, etc.; compounds of the type alkyl etherated amino resins, such as alkyl etherated derivatives of melaminic, ureic benzoguanaminic resins, of the methyl ether, butyl ether, isobutyl ether type, methyl-butyl mixed ethers and the like.

When an alkyl etherated amino resin is used as crosslinking agent, the ratio between the fluorinated polymer of the present invention and the amino resin is preferably between 55/45 and 95/5, more preferably between 60/40 and 90/10 by weight.

When a polyisocyanate is used as crosslinking agent, the ratio between the fluorinated polymer of the present invention and the polyisocyanate is preferably between 0.5 and 2, more preferably between 0.8 and 1.2 in terms of equivalents ratio between isocyanate groups and hydroxy groups.

Examples of crosslinking agents generally used when the functional group of the monomer (V) is the —NCO group, are compounds with at least two amino groups or two acid groups or two hydroxy groups.

Crosslinking occurs in any case at a temperature between the room temperature and 200° C., for a time about 30 minutes up to 24 hours.

In Table 1 hereinunder, the OH value is determined according to ASTM E222 standards, expressed by mg of KOH per gram of final resin. The acid value is determined according to ASTM D1639 standards.

EXAMPLE 1

Preparation of I) wherein $R_f$ has Formula II

In a 1 l flask 245 ml of methacrylic anhydride (1.54 moles), 0.5 g of hydroquinone, 1 ml of pyridine are charged and heated up to 80° C., then 820 g of fluorinated alcohol (III) with M.W. 709 (1.16 moles) are dripped in, the temperature being kept at the same value for 14 hours. The mixture is cooled to 50° C., 50 ml of methanol are introduced and stirring is continued for one hour. One distils at atmospheric pressure and then under vacuum (about 1 mm Hg) at 70° C.; 913 g of a cloudy liquid product are obtained. After filtration through a 0.45 micron membrane of PTFE, a limpid product is obtained, still containing, at 1H-NMR examination, hydrogenated impurities. The product is treated with perfluoroheptane and methanol; there are two phases: the lower phase mainly contains the methacrylate, without hydrogenated product, of formula $$CF_3O\ (C_3F_6O)_m(CF_2O)_n CF_2CH_2OCH_2CH_2OCOC(CH_3)\!=\!CH_2$$

with m/n=27.6 and M.W.=777 ($^{19}$F and $^1$H NMR analysis), obtained as residue at 50°–55° C./5 mbar.

EXAMPLE 2

Preparation of I) wherein $R_f$ has Formula II

In a 500 ml flask 0.5 moles of a fluorinated alcohol (III) of M.W. 550 are added in 4 hours to a mixture of 1 mole of methacryloyl chloride and 0.5 ml of pyridine, kept at 50° C. Gaseous HCl develops immediately. Reaction is continued still 30 minutes after the dripping is over, then methacryloyl chloride in excess is distilled with the boiler at 50°–60° C. under vacuum (about 10 mm Hg). 305 g of a slightly cloudy product are obtained, which are filtered through 0.45 micron membrane of PTFE: a colourless limpid product is obtained, represented by the formula $$CF_3O\ (C_3F_6O)_m(CF_2O)_n CF_2CH_2OCH_2CH_2OCOC(CH_3)\!=\!CH_2$$

with m/n=40 and M.W. 618 ($^1$H and $^{19}$F NMR analysis).

EXAMPLE 3

Preparation of I) wherein $R_f$ has Formula II

With the same technique of Example 2, one operates with a fluorinated alcohol (3) at M.W. 600; a colourless limpid product is obtained, represented by the formula $$CF_3O\ (C_3F_6O)_m(CF_2O)_n CF_2CH_2OCH_2CH_2OCOC(CH_3)\!=\!CH_2$$

with m/n=40 and M.W. 654 ($^1$H and $^{19}$F NMR analysis).

EXAMPLE 4

Preparation of I) wherein $R_f$ has Formula II)

With the same technique of Example 2, one operates with a fluorinated alcohol (III) at M.W. 650; a colourless limpid product is obtained, represented by the formula $$CF_3O\ (C_3F_6O)_m(CF_2O)_n CF_2CH_2OCH_2CH_2OCOC(CH_3)\!=\!CH_2$$

with m/n=40 and M.W. 702 ($^1$H and $^{19}$F NMR analysis).

EXAMPLE 5

Polymers of I)

100 g of methacrylate I of Example 2, 200 g of m-hexafluoroxylene and 0.1 g of AIBN are charged in a glass vial, cooled in a dry ice-acetone bath, degassed and sealed. The sealed vial is maintained in a thermostatic bath at the constant temperature of 60° C. for 8 hours; then the reaction mixture is poured into oil ether and the resulting precipitate is filtered and dried at 50° C. for 24 hours at a pressure of 10 mm Hg. 95 g of a transparent polymer are recovered.

EXAMPLE 6

Polymers of I)

With the same process of Example 5, 100 g of methacrylate of Example (IV) are polymerized; 93 g of transparent polymer are recovered.

EXAMPLE 7 (COMPARATIVE)

Polymers of I)

With the same modalities of Example 5, 100 g of methacrylate of the fluorinated alcohol (III) with p=0, with M.W.=550, are polymerized; 75 g of transparent polymer are recovered.

The yield is lower compared with Example 5.

EXAMPLE 8 (COMPARATIVE)

Polymers of I)

With the same modalities of Example 5, 100 g of methacrylate of the fluorinated alcohol (III) with p=0, with M.W.=650, are polymerized; 72 g of transparent polymer are recovered.

Same considerations for the yield as in Example 7 are valid.

EXAMPLE 9

Copolymers of I)

63 g (0.105 moles) of the methacrylate of Example 5, 27 g of MMA (0.27 moles), 200 g of MIBK and 1 g of AIBN are charged in a glass vial, cooled in a dry ice-acetone bath, degassed and sealed. The sealed vial is maintained in a thermostatic bath at the constant temperature of 60° C. for 8 hours. The reaction mixture is then poured into ligroin and the resulting precipitate is filtered and dried at 50° C. for 24 hours at the pressure of 10 mm Hg. 97 g of transparent polymer are recovered. The polymer is analyzed by $^{19}$F-NMR revealing that the molar composition between methacrylate of the fluorinated alcohol and MMA is 23/77. The polymer has an intrinsic viscosity of 0.98 dl/g, measured at the temperature of 35° C. by using m-hexafluoroxylene as solvent.

EXAMPLES 10–19

Preparation of the Resins 100 g of MIBK solvent are heated under nitrogen flow up to 105° C.; the polymerization initiator (AIBN) and the monomers mixture (100 g) having the composition shown in Table 1 are then added, in a period of 4 hours; and the polymerization is carried out at the same temperature for 2 hours.

EXAMPLES 20(1) TO 20(10)

Preparation of Coatings

On an aluminium support, treated with zinc phosphate, the compositions by grams reported in Table 2A are applied, left at room temperature for 5 minutes and then crosslinked according to the following modalities: for 30' at T=150° C. for examples 20(1), 20(4), 20(7) and 20(8); for 60' at T=80° C. for the remaining examples. Films of a 30 micron thickness are obtained. On the so obtained films the following evaluation tests reported in Table 2 B are carried out:

- MEK test: the surface of the coated sample is submitted to repeated rubbing by a pad soaked in MEK; the number of double strokes not causing removal of the film is reported;
- Adhesion according to ASTM D 3359 standard;
- Pencil hardness according to ASTM D 3363 standard;
- Bending test according to ASTM D 552 standard;
- Gloss according to ASTM D 523 standard;
- QUV test according to ASTM D 53 standard: UV cycles of 8 h at T=60° C., 4 h of condensation at T=40° C. The measurement is carried out after 1000 hours of exposure.

TABLE 1

| Composition | Examples | | | | | | | | | |
|---|---|---|---|---|---|---|---|---|---|---|
| | 10 | 11 | 12 | 13 | 14 | 15 | 16 | 17 | 18 | 19 |
| MMA (methylmethacrylate) | 26 | 51 | 41 | 41 | 38 | 58.5 | 40 | 40 | 40 | 40 |
| BMA (butylmethacrylate) | | | | | | | | 43.4 | | 44.4 |
| HEMA (hydroxy-ethylmethacrylate) | 11 | 11 | 9 | 9 | 8 | 7.5 | 15 | 15.6 | 15.6 | 15.6 |
| MAA (methacrylic acid) | | | | | | | 1 | 1 | | |
| (I) (of Example 2) | 63 | 58 | 50 | 50 | 54 | 34 | 34 | — | 44,4 | |
| AIBN | 1 | 1 | 1 | 2 | 3 | 3 | 2 | 2 | 2 | 2 |
| OH Value (KOH mg/resin g) | 45 | 44 | 38 | 38 | 34 | 32 | 72 | 67 | 68 | 67 |
| Acid Value (KOH mg/resin g) | 0 | 0 | 0 | 0 | 0 | 0 | 7.2 | 8 | 0 | 0 |
| Mn (GPC) (number average molecular weight) | 2000 | 16000 | 14500 | 9000 | 6300 | 8800 | 7200 | 8400 | 7000 | 8500 |

TABLE 2

A: Preparation

| Components | Examples | | | | | | | | | |
|---|---|---|---|---|---|---|---|---|---|---|
| | 20 (1) | 20 (2) | 20 (3) | 20 (4) | 20 (5) | 20 (6) | 20 (7) | 20 (8) | 20 (9) | 20 (10) |
| Example 10 | 70 | | | | | | | | | |
| Example 11 | | 86,8 | | | | | | | | |
| Example 12 | | | 88 | | | | | | | |
| Example 13 | | | | 70 | | | | | | |
| Example 14 | | | | | 89.4 | | | | | |
| Example 15 | | | | | | 90 | | | | |
| Example 16 | | | | | | | 70 | | | |
| Example 17 | | | | | | | | 70 | | |
| Example 18 | | | | | | | | | 81 | |
| Example 19 | | | | | | | | | | 81 |
| HMMM | 15 | | | 15 | | | 15 | 15 | | |
| N 3300 | | 6.6 | 6 | | 5.3 | 5 | | | 9.5 | 9.5 |
| Xylene | 15 | 6.6 | 6 | 15 | 5.3 | 5 | 15 | 15 | 9.5 | 9.5 |

HMMM = hexamethoxymethylmelamine
N3300 = hexamethylendiisocyanatetrimer

TABLE 2

| | B: Properties | | | | | | | | | |
|---|---|---|---|---|---|---|---|---|---|---|
| | Examples | | | | | | | | | |
| Composition | 20 (1) | 20 (2) | 20 (3) | 20 (4) | 20 (5) | 20 (6) | 20 (7) | 20 (8) | 20 (9) | 20 (10) |
| MEK Test | >100 | >100 | >100 | >100 | >100 | >100 | >100 | >100 | >100 | >100 |
| Adhesion | 100 | 100 | 100 | 100 | 100 | 100 | 100 | 95 | 100 | 95 |
| Hardness | F-2H | H-4H | F-3H | H-4H | F-2H | H-4H | H-5H | 2H-3H | HB-4H | 2H-3H |
| Bending test | passes | passes | passes | passes | passes | passes | passes | passes | passes | passes |
| Gloss | 80 | 83 | 86 | 85 | 80 | 85 | 85 | 86 | 84 | 85 |
| QUV: gloss retention % | 100 | 100 | 100 | 100 | 100 | 100 | 100 | 75 | 100 | 80 |

We claim:

1. Coatings obtained by the copolymerization of:

(a) 1–50% by weight of a monomer having a general formula:

$$YCF_2OR_fCFXCH_2(OCH_2CH_2)_pOCOCR=CH_2 \quad (I)$$

wherein:

Y is F, Cl, $CF_3$, $C_2F_5$, $C_3F_7$, or $C_4F_9$,

X is F or $CF_3$;

p is an integer from 1 to 5;

R is H or $CH_3$; and $R_f$ represents a radical having perfluoropolyethereal structure of average molecular weight of from 400 to 3000, formed by sequences of oxyfluoroalkylenic units, the sequences comprising units selected from the group consisting of:

—$CF_2O$—, —$CF_2CF_2O$—, —$CF_2CF_2CF_2O$—, $$-CF_2CFO-,\quad -CFO-,$$
$$\quad\quad\ |\quad\quad\quad\quad\ |$$
$$\quad\quad CF_3\quad\quad\quad CF_3$$

—$CF_2CF_2CH_2O$—,
and mixtures thereof;

(b) 40–90% by weight of one or more monomers having the formula:

$$CH_2=CR^1-COOA \quad (IV)$$

wherein:

$R^1$=H, $CH_3$, F, or Cl; and

A is an alkyl having from 1 to 12 carbon atoms or a fluoroalkyl having from 1 to 10 carbon atoms, or an aliphatic or aromatic cyclic group having from 6 to 8 carbon atoms; and (c) 2–30% by weight of one or more monomers having the formula:

$$CH_2=CR^2-CO-W-B \quad (V)$$

wherein:

$R^2$=H, $CH_3$, F, or Cl;

W=O or NH;

B=H or $(CH_2)_sB_1$, where:

s is 1 to 5, and $B_1$ is —COOH, —OH, —$CH_2CH_2$, NCO, —CO—$CH_2CO$—$CH_3$, or —$Si(OR^3)_3$, where $R^3$ is an alkyl group having 1 to 5 carbon atoms.

2. The coatings of claim 1, wherein the $R_f$ group is formed by CFXO and $$CF_2CFO$$
$$\ |$$
$$CF_3$$

units, where X is F or $CF_3$.

3. The coatings of claim 1, wherein the R group is $(C_3F_6)_m(CFXO)_n$, where m and n are integers and the ratio of m/n is greater than or equal to 2, and X is F or $CF_3$.

4. A topcoat comprising the coatings of claim 3.

* * * * *

UNITED STATES PATENT AND TRADEMARK OFFICE
CERTIFICATE OF CORRECTION

PATENT NO. : 5,623,037
DATED : April 22, 1997
INVENTOR(S) : Giovanni Simeone, et al.

It is certified that error appears in the above-identified patent and that said Letters Patent is hereby corrected as shown below:

Column 10, Line 33:  Delete:  "-$CH_2CH_2$,"
                     Insert:  ---$CH=CH_2$,--

Signed and Sealed this

Thirtieth Day of December, 1997

Attest:

BRUCE LEHMAN

Attesting Officer     Commissioner of Patents and Trademarks